US010406340B2

(12) United States Patent
Klepac

(10) Patent No.: US 10,406,340 B2
(45) Date of Patent: Sep. 10, 2019

(54) VASCULAR ACCESS PORT AND CATHETER

(75) Inventor: Steven R. Klepac, New Lenox, IL (US)

(73) Assignee: KAST AXESS, INC., New York, NY (US)

(*) Notice: Subject to any disclaimer, the term of this patent is extended or adjusted under 35 U.S.C. 154(b) by 891 days.

(21) Appl. No.: 13/222,462

(22) Filed: Aug. 31, 2011

(65) Prior Publication Data
US 2012/0116315 A1 May 10, 2012

Related U.S. Application Data

(60) Provisional application No. 61/411,270, filed on Nov. 8, 2010.

(51) Int. Cl.
A61M 39/00 (2006.01)
A61M 39/02 (2006.01)
A61M 39/06 (2006.01)
A61M 25/00 (2006.01)

(52) U.S. Cl.
CPC ........ *A61M 39/0247* (2013.01); *A61M 39/06* (2013.01); *A61M 25/0097* (2013.01); *A61M 2039/0258* (2013.01); *A61M 2039/0273* (2013.01); *A61M 2039/062* (2013.01)

(58) Field of Classification Search
CPC .......... A61M 39/0208; A61M 39/0247; A61M 2039/0211; A61M 2039/0258; A61M 2039/0261; A61M 1/1008; A61M 2039/0072; A61M 2039/0223; A61M 2039/027; A61M 2039/0282
USPC ..... 604/175, 513, 288.02, 539, 288.01, 533, 604/288.04, 502, 523
See application file for complete search history.

(56) References Cited

U.S. PATENT DOCUMENTS

| 3,461,869 | A | | 8/1969 | Hargest |
| 3,783,868 | A | | 1/1974 | Bokros |
| 3,788,328 | A | * | 1/1974 | Alley ................ A61M 25/0068 604/178 |
| 3,818,511 | A | * | 6/1974 | Goldberg ............ A61M 1/3655 264/257 |
| 3,826,257 | A | | 7/1974 | Buselmeier |
| 3,991,756 | A | | 11/1976 | Snyder |
| 3,998,222 | A | * | 12/1976 | Shihata ............... A61M 1/3655 604/175 |
| 4,092,983 | A | | 6/1978 | Slivenko |
| 4,318,401 | A | | 3/1982 | Zimmerman |
| 4,368,736 | A | * | 1/1983 | Kaster .................. A61B 17/11 606/153 |
| 4,400,169 | A | | 8/1983 | Stephen |

(Continued)

OTHER PUBLICATIONS

Search Report and Written Opinion for PCT/US2011/059708 dated Feb. 21, 2012.

*Primary Examiner* — William R Carpenter
(74) *Attorney, Agent, or Firm* — Duane Morris LLP

(57) ABSTRACT

A vascular access port and catheter for use in association with same. The port has a length greater than its height and an access face that is angled with respect to the longitudinal axis of the port. The catheter has a first end for association with a port, and a second end with an angled intra-vascular flange. Apart from the flange is an extra-vascular retaining ring. The wall of the vessel is disposed between the intra vascular flange and extra vascular retaining ring to hold the catheter in place without the need of sutures.

15 Claims, 3 Drawing Sheets

(56) References Cited

U.S. PATENT DOCUMENTS

| | | | | |
|---|---|---|---|---|
| 4,508,535 A | * | 4/1985 | Joh | A61M 1/3659 604/174 |
| 4,578,063 A | | 3/1986 | Inman et al. | |
| 4,668,222 A | | 5/1987 | Poirier | |
| 4,898,699 A | | 2/1990 | Tesio | |
| 5,092,850 A | * | 3/1992 | Buma | A61J 15/0015 604/175 |
| 5,163,952 A | * | 11/1992 | Froix | A61F 2/82 623/1.18 |
| 5,399,168 A | | 3/1995 | Wadsworth, Jr. et al. | |
| 5,456,714 A | * | 10/1995 | Owen | A61B 17/11 604/8 |
| 5,741,234 A | * | 4/1998 | Aboul-Hosn | A61B 17/3423 604/174 |
| 5,743,873 A | * | 4/1998 | Cai et al. | 604/288.02 |
| 5,755,780 A | * | 5/1998 | Finch et al. | 623/1.24 |
| 5,817,113 A | * | 10/1998 | Gifford, III | A61B 17/064 606/151 |
| 5,833,654 A | | 11/1998 | Powers et al. | |
| 6,007,576 A | * | 12/1999 | McClellan | A61F 2/064 623/23.64 |
| 6,042,569 A | | 3/2000 | Finch, Jr. et al. | |
| 6,053,901 A | | 4/2000 | Finch, Jr. et al. | |
| 6,056,717 A | | 5/2000 | Finch et al. | |
| 6,099,508 A | * | 8/2000 | Bousquet | A61M 39/0247 128/DIG. 26 |
| 6,213,973 B1 | | 4/2001 | Eliasen et al. | |
| 6,217,565 B1 | * | 4/2001 | Cohen | A61M 25/005 604/525 |
| 6,231,541 B1 | | 5/2001 | Kawamura | |
| 6,638,242 B2 | | 10/2003 | Wilson et al. | |
| 6,682,498 B2 | | 1/2004 | Ross | |
| 7,083,648 B2 | | 8/2006 | Yu et al. | |
| 7,182,771 B1 | * | 2/2007 | Houser | A61B 17/0644 606/154 |
| 7,803,143 B2 | | 9/2010 | Tallarida et al. | |
| 7,811,257 B2 | | 10/2010 | Saab | |
| 8,118,860 B2 | * | 2/2012 | Blomme | A61B 17/115 623/1.35 |
| 8,361,092 B1 | * | 1/2013 | Asfora | A61B 17/08 606/153 |
| 9,308,311 B2 | * | 4/2016 | Yevzlin | A61M 1/3655 |
| 9,572,917 B2 | * | 2/2017 | Marseille | A61M 1/12 |
| 2001/0004699 A1 | * | 6/2001 | Gittings | A61B 17/11 606/153 |
| 2003/0105517 A1 | * | 6/2003 | White | A61F 2/91 623/1.17 |
| 2004/0176739 A1 | | 9/2004 | Stephens et al. | |
| 2004/0199129 A1 | | 10/2004 | DiMatteo | |
| 2007/0225642 A1 | * | 9/2007 | Houser | A61B 17/0644 604/93.01 |
| 2008/0009803 A1 | | 1/2008 | Schon et al. | |
| 2008/0009936 A1 | * | 1/2008 | Kim | A61B 17/11 623/1.15 |
| 2008/0045894 A1 | | 2/2008 | Perchik et al. | |
| 2008/0249509 A1 | | 10/2008 | Glenn | |
| 2009/0023975 A1 | * | 1/2009 | Marseille | A61B 17/3421 600/16 |
| 2009/0099526 A1 | | 4/2009 | Powley et al. | |
| 2009/0118683 A1 | | 5/2009 | Hanson et al. | |
| 2009/0306599 A1 | * | 12/2009 | Furuzono | A61L 29/106 604/175 |
| 2010/0016835 A1 | | 1/2010 | Davey | |
| 2011/0066220 A1 | * | 3/2011 | Laguna | A61F 2/07 623/1.2 |
| 2011/0112567 A1 | * | 5/2011 | Lenker | A61M 25/0023 606/194 |
| 2011/0196298 A1 | * | 8/2011 | Anderson | A61M 25/0041 604/103.11 |
| 2012/0143141 A1 | * | 6/2012 | Verkaik | A61M 1/1008 604/175 |

\* cited by examiner

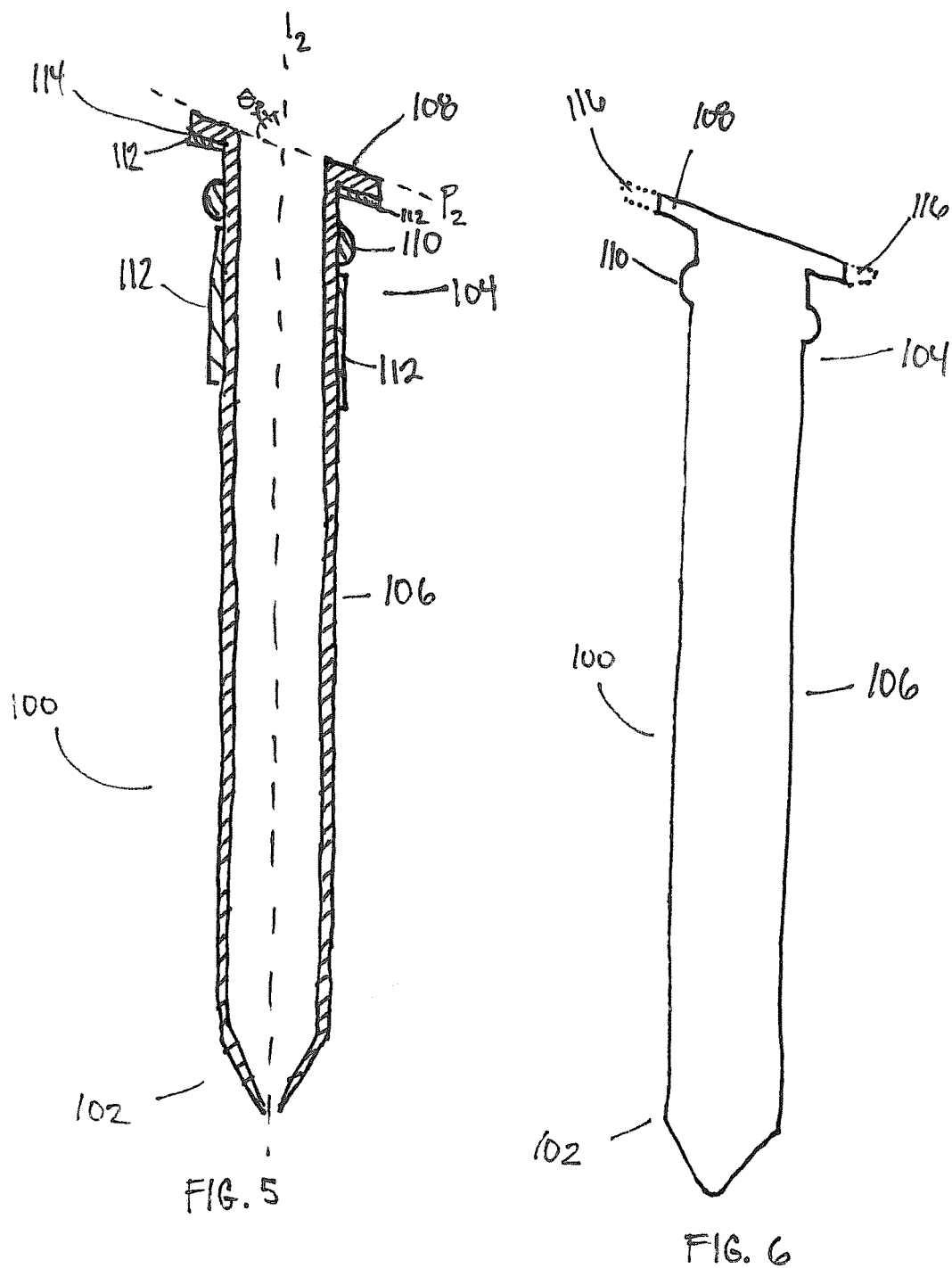

VASCULAR ACCESS PORT AND CATHETER

CROSS REFERENCE TO RELATED APPLICATIONS

This application claims priority from U.S. Provisional Application No. 61/411,270 filed Nov. 8, 2010, the entirety of which is incorporated herein.

FIELD OF THE INVENTION

The invention relates to a vascular access port and catheters that are used in association with same.

BACKGROUND OF THE INVENTION

Vascular access ports are useful in the treatment of certain diseases that can require the infusion of drugs, blood products, nutritional fluids, or other fluids into a patent's venous or arterial system.

The ports are beneficial in that they allow for repeated access to a patient's venous or arterial system through catheters attached to the port.

Since the ports are often implanted for an extended period of time, the manner of attachment, the comfort of the patient, and decreasing the rates of infections are all concerns that need to be adequately addressed by such a port.

With respect to the catheters used with the port, the catheters are typically attached to vessels using sutures or other invasive means that penetrate the vessel walls and can cause permanent damage to the vessel.

The present invention is directed to resolving these and other matters.

SUMMARY OF THE INVENTION

In one embodiment of the invention, the invention is directed to a port for allowing vascular access. The port may include a body having a length with a longitudinal axis and a height, the length being greater than the height, a first end having an access face and a second end with a connecting member, and, a retaining cuff disposed on the body at the first end, wherein the access face lies in a plane being at an angle with respect to the longitudinal axis of the body.

The port may include two fluidically separated chambers, and each chamber may be associated with a connecting member.

The port may include a perimeter about the longitudinal axis, and the perimeter may be an oval, or it may be a circle.

A port according to this embodiment allows for repeated access to the vessels, while providing increased stabilization of the position of the port. Moreover, the overall design is believed to provide for better patient comfort. Finally, such a port decreases the risk of infection as it is intended to be subcutaneously placed.

Further, it is believed that a port according to one or more of these embodiments allows the device to have a flatter (lower profile) position under the patient's skin. Moreover, such a port does not leave the access face outwardly exposed. In addition, it is believed to provide a better connection with a catheter, as the connection can be in line with the longitudinal axis of the port—as opposed to an angle.

In another embodiment of the invention, the invention is directed to a catheter having a first end capable of receiving a connecting member, a second end, and, a tubular extension disposed between the first end and second end and having a longitudinal axis, wherein the second end includes an intra-vascular flange, and a extra-vascular retaining ring being spaced apart from the intravascular flange, and, wherein the intra-vascular flange is in a plane located at an angle to the longitudinal axis.

The extra-vascular retaining ring may be integral with the tubular extension.

Further, the extra-vascular retaining ring may be movable with respect to the intra-vascular flange.

The catheter may also include a stent material disposed adjacent the second end.

The intra-vascular flange may also include a stent material, and may include a stent material on an upper-side of the intra-vascular flange.

The edges of the intra-vascular flange may be tapered.

A catheter according to one or more of these embodiments is believed to provide many benefits. For example, a catheter according to the present invention does not need to be sutured to a vessel. Rather, the vessel wall is placed between the intra-vascular flange and the extra-vascular retaining ring. This holds the catheter in place. Since the catheter does not require sutures, or other invasive attaching means, less damage is done to vessel wall.

Moreover, since no continuous arterial venous fistula is created, the return vein will not develop pressure induced intimal hyperplasia or stenosis. While, some fibrin deposition will occur from the presence of the catheter material at the anastomotic site, this should progress in a much slower manner.

In addition, lack of a continuous fistula also minimizes the possibility of the patient developing an arterial steal phenomena or extremity swelling from passive venous congestion.

The maintenance of the port and catheters can also easily be achieved with such a port and/or catheter.

Moreover the port and catheters allow for central vascular access can be obtained for antegrade arterial and retrograde venous cannulation to perform thrombectomy and angioplasty. When a catheter needs to be exchanged, secondary sites can be utilized in close proximity to the original anastomosis. This extends the life of the accessed vessel and thus markedly extends the time an extremity can be used for dialysis.

It is contemplated, but not necessarily required, that a port according to the present invention is utilized in association with a catheter according to the present invention.

It is to be understood that the aspects and objects of the present invention described above may be combinable and that other advantages and aspects of the present invention will become apparent upon reading the following description of the drawings and detailed description of the invention.

BRIEF DESCRIPTION OF THE DRAWINGS

The present invention will become more fully apparent from the following description and appended claims, taken in conjunction with the accompanying drawings.

FIG. 5 is a side cutaway view of a catheter according to the present invention.

FIG. 6 is a side view of a catheter according to the present invention.

Figure 1:
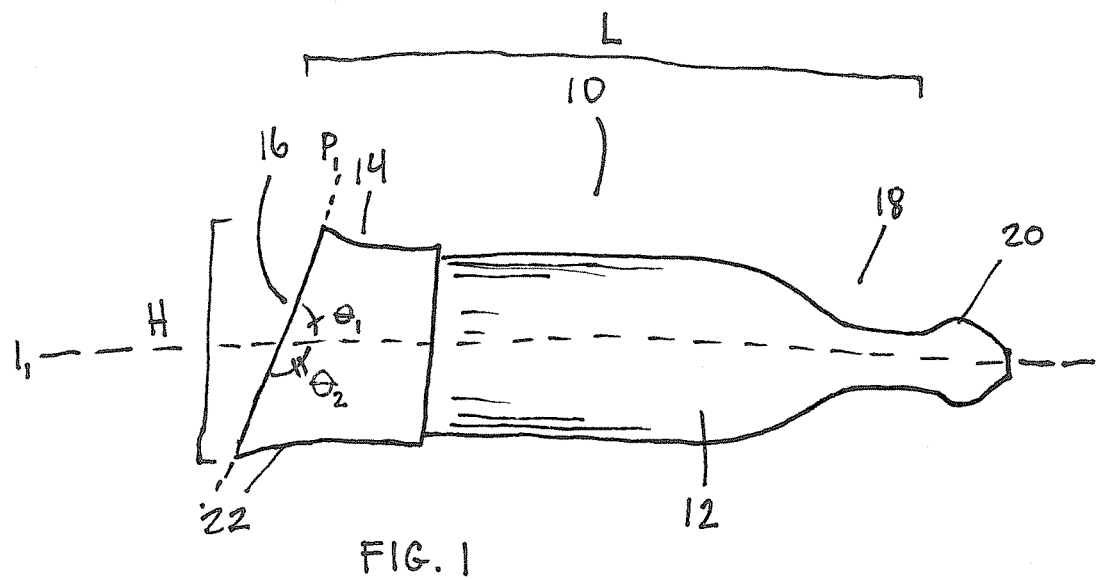
FIG. 1 is a side perspective view of a vascular access port according to an embodiment of the present invention.

Understanding that the accompanying drawings depict only typical embodiments, and are, therefore, not to be considered to be limiting of the scope of the present disclosure, the embodiments will be described and explained with specificity and detail in reference to the accompanying drawings.

DETAILED DESCRIPTION OF THE DRAWINGS

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

Reference throughout this description to features, advantages, objects or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

A preferred embodiment of the port 10 according to an aspect of the present invention includes a body 12 having a first end 14 and a second end 18. The body 12 may be constructed out of plastic, titanium, or any other suitable material.

Measuring from the first end 14 to the second end 18 provides a measurement for a length L. The body 12 also includes a height H. The length L is greater than the height H. Depending on the configuration of the body 12, the length L may range between 2.5 cm-3.8 cm and the height H may range from 1.3 cm-1.9 cm. This configuration allows for the port 10 to be implanted in a patient, such that the length L of the body 12 is relatively parallel to the body part in the patient where the port 10 is being implanted. For example, if the port 10 is implanted in an arm, the length L of the body 12 would extend in the same direction as the length of the patient's arm.

The first end 14 includes an access face 16 that lies in a plane $P_1$ that is at an angle with respect to the longitudinal axis $l_1$ of the body 12. It is preferred that the acute angle $\theta_1$ of the access face 16 be disposed adjacent the patient's skin (or laterally), and the obtuse angle $\theta_2$ be disposed away from the skin (or medially). At the second end 18, it is preferred that the body 12 is tapered to a connecting member 20. The connecting member allows for a catheter 50 or other device to be attached to the body 12 of the port 10 in order to, for example, transport liquids deposited by needle.

The access face 16 may include a septum 24 for allowing access to a chamber 26 inside of the body 12. In this manner, the septum 24 can be penetrated, for example, by a needle and allow for delivery of liquid. The septum 24 provides for a fluidically sealed chamber 26. The septum 24 may be made from silicone or other suitable materials.

In order to maintain the placement of the port 10, disposed about the first end 14 is a retaining cuff 22. The retaining cuff 22 allows for tissue to grow and attach itself to the retaining cuff 22, and thus the port 10. This will maintain the position of the port 10 within the patient's body. For example, the retaining cuff 22 may be Dacron®, a polyester weave material, or any other known material. Other retaining methods known in the art, such as sutures, etc, may be employed to assist in maintaining the position of the port 10.

In one embodiment contemplated, a port 60 may include two fluidically separated chambers 26a, 26b, and each chamber 26a, 26b may be associated with a connecting member 20a, 20b. (See, FIG. 4). In such a configuration, it is contemplated that nipples 62, ridges, studs, or other structures are provided such that the structure indicates the appropriate configuration. In other words, nipples 62 may be placed on the external surface of the body on the medial side so that after subcutaneous implantation, so that a person can feel the nipples 62 and easily discern which chamber 26a, 26b is disposed medially.

Figure 2:
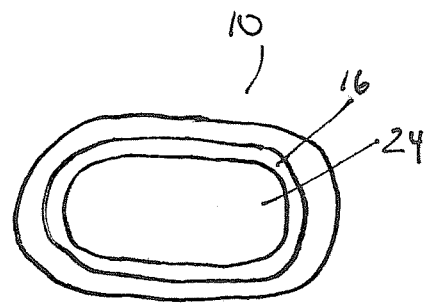
FIG. 2 is a front perspective view of a vascular access port according to an embodiment of the present invention.
Figure 3:
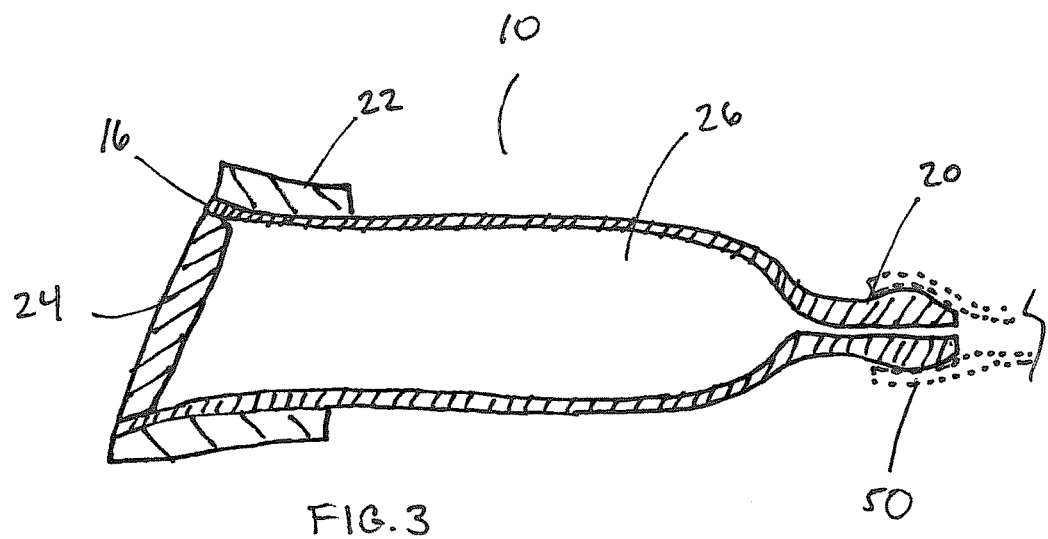
FIG. 3 is a side perspective cutaway view of a vascular access port according to an embodiment of the present invention.
Figure 4:
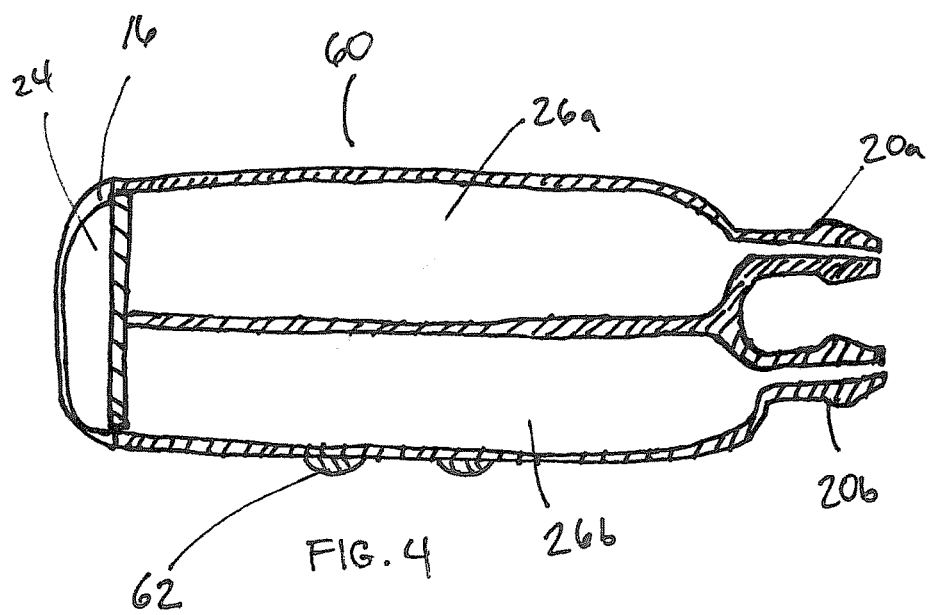
FIG. 4 is a top perspective cutaway view of a vascular access port according to an embodiment of the present invention.

The port 10, 60 may include a perimeter about the longitudinal axis, and the perimeter may be an oval (FIG. 2), or it may be a circle (FIG. 4). Although depicted with a dual chamber port 60 having a circle perimeter and the single chamber port 10 having an oval perimeter, the present invention is not indented to be limited to such a shape, and the port 10, 60 may have various shapes and still fall within the scope of the present invention.

As previously discussed, a port according to one or more aspects of the present invention is believed to provide, at a minimum, a port that minimizes the risk of infection, while providing an access point that accommodates the patient's comfort, as well as maintaining its implanted positioning.

As previously mentioned, the connecting member 20 allows the port 10, 60 to be attached to, for example, a catheter 50. It is preferred, but not required, that the catheter 100 be of the configuration depicted in FIGS. 5-6.

In this aspect of the invention, the catheter 100 includes a first end 102 capable of receiving a connecting member, a second end 104, and, a tubular extension 106 disposed between the first end 102 and second end 104. The catheter 100 also includes a longitudinal axis $l_2$. The catheter 100 may be made from polyurethane. Moreover, the size of the catheter 100 can range from 5 F to 8 F.

The second end 104 includes an intra-vascular flange 108, and a extra-vascular retaining ring 110 being spaced apart from the intravascular flange 108.

The intra-vascular flange 108 is in a plane $P_2$ located at an angle $\theta_3$ to the longitudinal axis $l_2$. In a preferred embodiment, the intra-vascular flange 108 has an angle $\theta_3$ between 30-45 degrees to the longitudinal axis $l_2$.

The extra-vascular retaining ring 110 may be integral with the tubular extension 106.

Further, the extra-vascular retaining ring 110 may be movable with respect to the intra-vascular flange 108.

As shown in FIG. 5 the catheter 100 may also include a sleeve of stent material 112 disposed adjacent the second end 103. One such stent material 112 is nitinol.

The intra-vascular flange 108 may also include a stent material 112, and may include a stent material 112 on an upper-side 114 of the intra-vascular flange 108. Another suitable stent material 112 may be stent barbs.

Further, the edges 116 of the intra-vascular flange 108 may be tapered to assist in the placement of same with guide wires. These guide wires may be removed prior to attachment of the catheter 100 to the port 10.

The catheter 100 should have some structural rigidity which can be a property of the material of the catheter 100 (or thickness of same), or it may be imparted from an additional material, for example, wire mesh, or a coating such as silver oxide.

In order to aid in the placement of the catheter 100, it is contemplated that the intravascular flange 108 and the extra-vascular retaining ring 110 are radio opaque. The catheter 100 may be positioned within vessels with the aide of a peel-away sheath of retractable stent deployment device.

As discussed above, the intra-vascular flange 108 and the extra-vascular retaining ring 110 function to hold the vessel wall, such that the catheter 100 may be placed without the need for suturing to the vessel wall. This will result in less damage done to the vessel.

It is to be understood that additional embodiments of the present invention described herein may be contemplated by one of ordinary skill in the art and that the scope of the present invention is not limited to the embodiments disclosed. While specific embodiments of the present invention have been illustrated and described, numerous modifications come to mind without significantly departing from the spirit of the invention, and the scope of protection is only limited by the scope of the accompanying claims.

What is claimed is:

1. A catheter comprising:
    a tubular extension extending from a first end to a second end and defining a longitudinal axis between the first end and the second end, wherein the first end is configured to receive a connecting member and wherein the diameter of the tubular extension is in the range from 5 French to 8 French;
    an intra-vascular flange formed from a first material and coupled to the tubular extension at the second end, the intra-vascular flange having a planar lower face and a planar upper face, the planar lower face and the planar upper face being parallel to one another and non-orthogonal with respect to the longitudinal axis;
    an extra-vascular retaining ring movable with respect to the intra-vascular flange along the tubular extension;
    an annular disk formed from a second material coupled to the planar upper face of the intra-vascular flange, the second material being different from the first material such that the annular disk is configured to increase the rigidity of the intra-vascular flange;
    wherein the extra-vascular retaining ring and the intra-vascular flange are configured to hold the catheter in place when a wall of a peripheral vessel is positioned between them in the absence of sutures; and
    a sleeve of stent material which is directly coupled to only an outer surface of the tubular extension such that the sleeve terminates at a sleeve distal end and a sleeve proximal end whereby the entirety of the sleeve lies between the extra-vascular retaining ring and the first end of the tubular extension.

2. The catheter of claim 1, wherein the extra-vascular retaining ring has a hemispherical cross-section.

3. The catheter of claim 1, wherein the intra-vascular flange includes tapered edges to assist in the placement of the intra-vascular flange with guide wires.

4. The catheter of claim 1, wherein the angle between the plane defined by the planar lower face of the intra-vascular flange and the longitudinal axis is between 30° and 45°.

5. The catheter of claim 1, wherein the distal end of the sleeve is adjacent the extra-vascular retaining ring.

6. The catheter of claim 5, wherein the sleeve comprises a stent material comprising nitinol.

7. The catheter of claim 1, wherein the annular disk is constructed of a stent material comprising stent barbs.

8. The catheter of claim 1, wherein an inner face of the annular disk abuts the tubular extension and an outer face of the annular disk is adjacent an outer edge of the intra-vascular flange.

9. The catheter of claim 1, wherein the extra-vascular retaining ring circumscribes the tubular extension.

10. A catheter comprising:
    a tubular extension extending from a first end to a second end and defining a longitudinal axis between the first end and the second end, wherein the first end is configured to receive a connecting member and wherein the diameter of the tubular extension is in the range from 5 French to 8 French;
    an intra-vascular flange formed from a first material and coupled to the tubular extension at the second end of the tubular extension, the intra-vascular flange being non-orthogonal to the longitudinal axis and having an upper face and a lower face, wherein the upper face is nearer the first end than is the lower face;
    an extra-vascular retaining ring coupled to the tubular extension and movable along the longitudinal axis of the tubular extension;
    an annular disk coupled to the upper face of the intra-vascular flange; and
    a sleeve of stent material which is directly coupled to only an outer surface of the tubular extension such that the sleeve terminates at a sleeve distal end and a sleeve proximal end whereby the entirety of the sleeve lies between the extra-vascular retaining ring and the first end of the tubular extension;
    wherein the extra-vascular retaining ring and the intra-vascular flange are configured to hold the catheter in place when a wall of a peripheral vessel is positioned between them in the absence of sutures.

11. The catheter of claim 10, wherein the distal end of the sleeve is adjacent the extra-vascular retaining ring.

12. The catheter of claim 10, wherein the sleeve comprises a stent material comprising nitinol.

13. The catheter of claim 10, wherein the annular disk is constructed of a stent material comprising stent barbs.

14. The catheter of claim 10, wherein an inner face of the annular disk abuts the tubular extension and an outer face of the annular disk is adjacent an outer edge of the intra-vascular flange.

15. The catheter of claim 10, wherein the extra-vascular retaining ring circumscribes the tubular extension.

* * * * *